US 7,262,047 B2

(12) United States Patent
Venkateswaran

(10) Patent No.: US 7,262,047 B2
(45) Date of Patent: Aug. 28, 2007

(54) *BACILLUS PUMILUS* SAFR-032 ISOLATE

(75) Inventor: Kasthuri J. Venkateswaran, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/124,414

(22) Filed: May 6, 2005

(65) Prior Publication Data

US 2005/0272139 A1    Dec. 8, 2005

Related U.S. Application Data

(60) Provisional application No. 60/568,740, filed on May 6, 2004.

(51) Int. Cl.
*C12N 1/20* (2006.01)
(52) U.S. Cl. .................................. 435/252.5; 435/832
(58) Field of Classification Search ..................... None
See application file for complete search history.

(56) References Cited

OTHER PUBLICATIONS

Anonymous. 1980. NASA standard procedures for the microbiological examination of space hardware NHB 5340.1B.
Anonymous, 2000, "Preventing the Forward Contamination of Europa," National Academies Press, Washington DC.
Appelbaum, J., and D. J. Flood. 1990. Solar-Radiation on Mars. Solar Energy 45:353-363.
Arvidson, R., et al., 2004. Localization and physical property experiments conducted by opportunity at Meridiani Planum. Science 306:1730-1733.
Arnold, R.J., et al., 1998, "Fingerprint matching of *E. coli* strains with matrix-assisted laser desorption ionization time-of-flight mass spectrometry of whole cells using a modified correlation approach," Rapid Commun. Mass Spectrom. 12, 630-636.
Bright, J.J., et al., 2002, "Rapid typing of bacteria using matrix-assisted laser desorption ionization time-of-flight mass spectrometry and pattern recognition software," J. Microbiol. Methods 48, 127-138.
Busse, H.J, et al., 1996, "Classification and identification of bacteria: current approaches to an old problem," Overview of methods used in bacterial systematics. J. Biotechnol. 47, 3-38.
Cockell, C. S., D. C. Catling, W. L. Davis, K. Snook, R. L. Kepner, P. Lee, and C. P. McKay, 2000. The ultraviolet environment of Mars: biological implications past, present, and future. Icarus 146:343-59.
Cospar. 1992. Task Group on Planetary Protection, Space Studies Board, National Research Council (U.S.). National Academy of Sciences.
Dickinson, D.N., et al., 2004, "Species differentiation of a diverse suite of *Bacillus* spores using mass spectrometry based protein profiling," Appl. Environ. Microbiol. 70, 475-482.
Elhanany, E., et al., 2001, "Detection of specific *Bacillus antracis* spore biomarkers by matrix-assisted laser desorption/ionization time-of-flight mass spectrometry," Rapid Commun Mass Spectrom. 15, 2110-2116.
Ezaki, T., 1989, "Fluorometric deoxyribonucleic acid deoxyribonucleic acid hybridization in micro-dilution wells as an alternative to membrane-filter hybridization in which radioisotopes are used to determine genetic relatedness among bacterial strains," Int. J. Syst. Bacteriol. 39, 224-229.
Fenselau, C., et al., 2001, "Characterization of intact microorganisms by MALDI mass spectrometry," Mass Spectrom. Rev. 20, 157-171.
Hathout, Y., et al., 1999, "Identification of *Bacillus* spores by matrix-assisted laser desorption ionization-mass spectrometry," Appl. Environ. Microbiol. 65, 4313-4319.
Horneck, G., H. Bucker, K. Dose, K. D. Martens, A. Bieger, H. D. Mennigmann, G. Reitz, H. Requardt, and P. Weber. 1984. Microorganisms and biomolecules in space environment experiment ES 029 on Spacelab-1. Advances in Space Research 4:19-27.
Horneck, G., H. Buckner, and G. Reitz. 1994. Long-term survival of bacterial spores in space. Advances in Space Research 14:41-5.
Horneck, G., P. Rettberg, G. Reitz, J. Wehner, U. Eschweiler, K. Strauch, C. Panitz, V. Starke, and C. Baumstark-Khan. 2001. Protection of bacterial 21 spores in space, a contribution to the discussion on Panspermia. Origins of Life and Evolution of the Biosphere 31:527-547.
Hoyer, O (2000) The status of UV technology in Europe. IUVA News 2: 22-27.
Jarman, K.H., et al., 1999, "Extracting and visualizing matrix-assisted laser desorption/ionization time-of-flight mass spectral fingerprints," Rapid Commun. Mass Spectrom. 13, 1586-1594.
Kempf, M., F. Chen, R. Kern, and K. Venkateswaran. 2004. Recurrent isolation of hydrogen peroxide-resistant spores of *Bacillus pumilus* from a spacecraft assembly facility (In press), Astrobiology.
Kuhn, W. R., S. R. Rogers, and R. D. Macelroy. 1979. Response of Selected Terrestrial Organisms to the Martian Environment—Modeling Study. Icarus 37:336-346.
Lay, J.O., 2001, "MALDI-TOF mass spectrometry of bacteria," Mass Spectrom. Rev. 20, 172-194.
La Duc, M. T., W. Nicholson, R. Kern, and K. Venkateswaran. 2003. Microbial characterization of the Mars Odyssey spacecraft and its encapsulation facility. Environmental Microbiology 5:977-985.
La Duc, M. T., M. Satomi, N. Agata, and K. Venkateswaran. 2004. gyrB as a phylogenetic discriminator for members of the *Bacillus anthracis*-cereusthuringiensis group. Journal of Microbiological Methods 56:383-394.

(Continued)

*Primary Examiner*—David M. Naff
*Assistant Examiner*—Deborah K. Ware
(74) *Attorney, Agent, or Firm*—Tope-McKay & Associates

(57) ABSTRACT

The present invention relates to discovery and isolation of a biologically pure culture of a *Bacillus pumilus* SAFR-032 isolate with UV sterilization resistant properties. This novel strain has been characterized on the basis of phenotypic traits, 16S rDNA sequence analysis and DNA-DNA hybridization. According to the results of these analyses, this strain belongs to the genus *Bacillus*. The GenBank accession number for the 16S rDNA sequence of the *Bacillus pumilus* SAFR-032 isolate is AY167879.

1 Claim, 4 Drawing Sheets

OTHER PUBLICATIONS

La Duc, M. T., Satomi, and K. Venkateswaran. 2004. *Bacillus odysseyi* sp. nov., a round-spore-forming *Bacillus* isolated from the Mars Odyssey spacecraft. International Journal of Systematic and Evolutionary Microbiology 54:195-201.

La Duc, M.T., et al., 2004, "Microbial monitoring of spacecraft associated environments," Microb. Ecol. (in press). DOI:10.1007/s00248-003-1012-0.

Logan, N.A., 1994, "Bacterial Systematics," Blackwell, Oxford.

Link, L., J. Sawyer, K. Venkateswaran, and W. Nicholson. 2003. Extreme spore UV resistance of *Bacillus pumilus* Isolates obtained from an ultraclean spacecraft assembly facility. Microbial Ecology 47:159-163.

Mileikowsky, C, Cucinotta, FA, Wilson, JW, Gladman, B, Horneck, G, Lindegren, L, Melosh, HJ, Rickman, H, Valtonen, M, Zheng, JQ (2000) Natural transfer of viable microbes in space. Part 1: From Mars to Earth and Earth to Mars. Icarus 145: 391-427.

Nicholson, WL (2003) Using thermal inactivation kinetics to calculate the probability of extreme spore longevity: implications for paleomicrobiology and lithopanspermia. Orig Life Evol Biosphere 33, 621-631, 2003.

Nicolson, WL, Law, JF (1999) Method for purification of bacterial endospores from soils: UV 2 resistance of natural Sonoran desert soil populations of *Bacillus* spp. with reference to *B. subtilis* strain 168. J Microbiol Methods 35: 13-21.

Nicholson, W. L., and B. Gateano. 2003. UV resistance of *Bacillus anthracis* spores revisited: validation of *Bacillus subtilis* spores as UV surrogates for spores of *B. anthracis* Sterne. Applied and Environmental Microbiology 69:1327-1330.

Nicholson, W. L., N. Munakata, G. Horneck, H. J. Melosh, and P. Setlow. 2000. Resistance of *Bacillus* endospores to extreme terrestrial and extraterrestrial environments. Microbiology and Molecular Biology Reviews 64:548-572.

Nicholson, W. L., B. Setlow, and P. Setlow. 2002. UV photochemistry of DNA in vitro and in *Bacillus subtilis* spores at Earth-ambient and low atmospheric pressure: Implications for spore survival on other planets or moons in the solar System. Astrobiology 2:417-425.

Popham, D. L., B. Illades-Aguiar, and P. Setlow. 1995. The *Bacillus subtilis* dacB gene, encoding penicillin-binding protein 5*, is part of a three-gene operon required for proper spore cortex synthesis and spore core dehydration, Journal of Bacteriology 177:4721-9.

Riesenman, P. J., and W. L. Nicholson. 2000. Role of the spore coat layers in *Bacillus subtilis* spore resistance to hydrogen peroxide, artificial UV-C, UV-B, and solar UV radiation. Applied and Environmental Microbiology 66:620-626.

Rummel, J. D. 2001. Planetary exploration in the time of astrobiology: protecting against biological contamination. Proceedings of the National Academy of Sciences of the United States of America 98:2128-31.

Ryzhov, V., et al., 2000, "Rapid characterization of spores of *Bacillus cereus* group bacteria by matrix-assisted laser desorption-ionization time-of-flight mass spectrometry," Appl. Environ. Microbiol. 66, 3828-3834.

Saitou, N., et al, 1987, "The neighbor-joining method—a new method for reconstructing phylogenetic trees," Mol. Biol. Evol. 4, 406-425.

Sambrook, J., et al., 1989, "Molecular Cloning, A Laboratory Manual," 2nd ed. Cold Spring Harbor Laboratory, Cold Spring Harbor, NY.

Schaeffer, P., J. Millet, and J. P. Aubert. 1965. Catabolic repression of bacterial sporulation. Proceedings of the National Academy of Sciences of the United States of America 54:704-11.

Schuerger, A. C., R. L. Mancinelli, R. G. Kern, L. J. Rothschild, and C. P. McKay. 2003. Survival of endospores of *Bacillus subtilis* on spacecraft surfaces under simulated Martian environments: implications for the forward contamination of Mars. Icarus 165:253-276.

Setlow, B., and P. Setlow. 1995. Binding to DNA protects alpha/beta-type, small, acid-soluble spore proteins of *Bacillus* and *Clostridium* species against digestion by their specific protease as well as by other proteases. J Bacteriol 177:4149-51.

Satomi, M., et al., 1998, "Tetra-genococcus muriaticus sp. nov., a new moderately halophilic lactic acid and bacterium isolated from fermented squid liver sauce," Int. J. Syst. Bactriol. 48, 332.

Swofford, D., 1990, "PAUP: Phylogenetic Analysis using Parsimony [3.0]," Illinois Natural History Survey, Champaign, IL, USA.

Thomas-Keprta, KL, Clemett, SJ, Bazylinski, DA, Kirschvink, JL, McKay, DS, Wentworth, SJ, Vali, H, Gibson, Jr EK, Romanek, CS (2003) Magnetofossils from ancient Mars: a robust biosignature in the martian meteorite ALH84001. Appl Environ Microbiol 68: 3663-3672.

Tomasko, M., L. Doose, M. Lemmon, P. Smith, and E. Wegryn. 1999. Properties of dust in the martian atmosphere from the imager on Mars pathfinder. Journal of Geophysical Research-Planets 104:8987-9007.

Venkateswaran, K., N. Hattori, M. T. La Duc, and R. Kern. 2003. ATP as a biomarker of viable microorganisms in clean-room facilities. Journal of Microbiological Methods 52:367-377.

Venkateswaran, K., M. Kempf, F. Chen, M. Satomi, W. Nicholson, and R. Kern. 2003. *Bacillus nealsonii* sp. nov., isolated from a spacecraft-assembly facility, whose spores are gamma-radiation resistant. International Journal of Systematic Bacteriology 53:165-172.

Yamamoto, S., et al., 1996, "Phylogenetic analysis of Acinetobacter strains based on the nucleotide sequences of gyrB genes and of the amino acid sequences of their products," Int. J. Syst. Bacteriol. 46, 506-511.

Xue, Y., and W. L. Nicholson. 1996. The two major spore DNA repair pathways, nucleotide excision repair and spore photoproduct lyase, are sufficient for the resistance of *Bacillus subtilis* spores to artificial UV-C and UV-B but not to solar radiation. Applied and Environmental Microbiology 62:2221-2227.

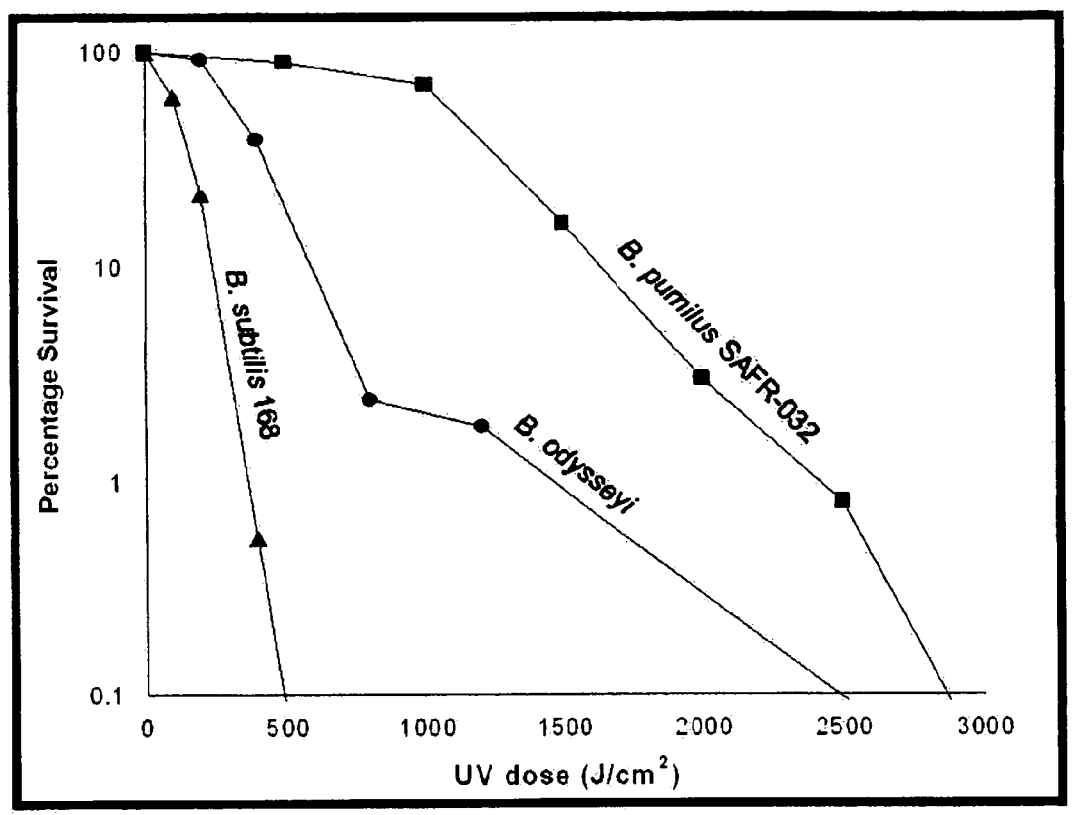
Figure 1. Dose response curve for 3 *Bacillus* species.

Figure 2. Resistance of 3 strains of *Bacillus* to UV radiation at the Mars solar constant.

Figure 3. Protection of *B. subtilis* by SAFR-32 from full spectrum irradiation at the Mars solar constant.

Scanning electron micrograph of *B. pumilus* SAFR-032 spores

Light microscope photograph of *B. pumilus* SAFR-032 cells

Transmission electron micrograph of a *B. pumilus* SAFR-032 spore

BACILLUS PUMILUS SAFR-032 ISOLATE

PRIORITY CLAIM

This application is a non-provisional application, claiming the benefit of priority to provisional application No. 60/568,740, filed in the United States on May 6, 2004, entitled "UV Resistant *Bacillus pumilus* SAFR-032."

GOVERNMENT RIGHTS

The invention described herein was made in the performance of work under a NASA contract, and is subject to the provisions of Public Law 96-517 (35 U.S.C. 202) in which the Contractor has elected to retain title.

FIELD OF INVENTION

The present invention relates to an isolated biologically pure culture of a novel spore forming *Bacillus* species, and more particularly, to a *Bacillus pumilus* SAFR-032 isolate with high sterilization resistant properties.

BACKGROUND OF INVENTION

Several physiologically and phylogenetically distinct microorganisms have been encountered while examining microbial contamination of spacecraft surfaces. Some of these micro-organisms form round, exosporium-bearing spores, whose exosporia might be responsible for adaptation to the extreme clean conditions of, and direct adhesion to, spacecraft surfaces.

Such biofouling is a concern in not only space travel, but in a number of industries. Isolation, identification and understanding of the highly resistant and adhesive micro-organisms could be of significant use in industry, where biofouling is a major cause of reduction in productivity (resulting in a loss of over $6.5 billion in marine industries alone), and in medicine, where bacterial adhesion is often a primary step in human disease. In addition, purified exosporium components (proteins, lipids, etc.) could possibly be used in other ways, such as in sunscreens or to prolong the lives of convertible tops, tents, etc. as an Ultra Violet-ray retardant spray.

Additionally, isolation of the microorganism would allow for formation of strategies for inactivating those resistance characteristics that interfere with sterilization of spacecraft materials; in particular, resistance to Hydrogen Peroxide ($H_2O_2$), Ultra Violet (UV), and g-radiation and adhesion. An understanding of these mechanisms will guide the development of sterilization procedures that are targeted to the specific molecules responsible for resistance, and could eliminate the need for unduly harsh methods that jeopardize equipment. A need exists for highly resistant bacterial isolates to study further to create an improved sterilization procedure that would enable spacecraft to meet planetary protection requirements without a terminal heat sterilization step. This would support implementation of planetary protection policies for life detection missions.

SUMMARY OF INVENTION

The present invention relates to an isolated biologically pure culture of a novel spore forming *Bacillus* species, and more particularly, to a *Bacillus pumilus* SAFR-032 isolate with high sterilization resistant properties, having a GenBank accession number of AY167879.

Additionally, because of its UV resistant properties, purified exosporium components (proteins, lipids, etc.) of *B. pumilus* SAFR-032 could be used in sunscreens or to prolong the lives of convertible tops, tents, etc. as a UV-ray retardant spray.

BRIEF DESCRIPTION OF THE DRAWINGS

The objects, features and advantages of the present invention will be apparent from the following detailed descriptions of the various aspects of the invention in conjunction with reference to the following drawings, where:

FIG. 1 is a chart illustrating UV does response curves for three *Bacillus* species;

FIG. 2 is chart illustrating relative resistance of three strains of *Bacillus* to UV radiation at the Mars solar constant;

FIG. 3 is a chart illustrating the protection of *B. subtilis* by SAFR-032 from full spectrum irradiation at the Mars solar constant;

Figure 4:
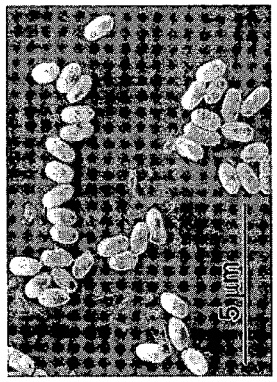
FIG. 4 is scanning electron microscopy image of *Bacillus pumilus* SAFR-032 spores.

Appendix A is an article co-authored by an inventor of the present invention, discussing *Bacillus pumilus* SAFR-032, entitled, "survival of spacecraft-associated microorganisms under simulated Martian UV irradiation;"

Appendix B is an article co-authored by an inventor of the present invention, discussing the identification and classification of *Bacillus pumilus* spores, entitled, "MALDI-TOFMS compared with other polyphasic taxonomy approaches for the identification and classification of *Bacillus pumilus* spores;" and Appendix C is an article co-authored by an inventor of the present invention, discussing the UV resistance of *Bacillus pumilus* isolates, entitled, "extreme spore UV resistance of *Bacillus pumilus* isolates obtained from an ultraclean spacecraft assembly facility."

DETAILED DESCRIPTION

The present invention relates to an isolated biologically pure culture of a novel spore forming *Bacillus* species, and more particularly, to a *Bacillus pumilus* SAFR-032 isolate with high UV and sterilization resistant properties.

The following description, taken in conjunction with the referenced drawings and/or tables, is presented to enable one of ordinary skill in the art to make and use the invention. Various modifications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein. Furthermore, it should be noted that unless explicitly stated otherwise, the figures included herein are illustrated qualitatively and without any specific scale, and are intended to generally present the concept of the present invention.

In order to provide a working frame of reference, first a glossary of terms used in the description and claims is given as a central resource for the reader. Next, a discussion of various aspects of the present invention is provided to give an understanding of the specific details.

(1) Glossary

Before describing the specific details of the present invention, a centralized location is provided in which various terms used herein and in the claims are defined. The glossary provided is intended to provide the reader with a general understanding for the intended meaning of the terms, but is not intended to convey the entire scope of each term. Rather, the glossary is intended to supplement the rest of the specification in more clearly explaining the terms used.

16S rDNA—The term "16S rDNA" refers to codes for a small subunit of ribosomal RNA. The 16S rDNA is now the most widely used informational macromolecule for bacterial systematic studies at the family, genus, species, and subspecies levels. The 16S rDNA contains conserved sequences that can be used to infer natural relationships between distantly related species and variable regions that can be used to separate closely related ones.

API 20NE Test Strips—The term "API 20NE" refers test strips that are used for 24-48 hour identification of gram-negative Enterobacteriaceae.

DNA-DNA hybridization—The term "DNA-DNA hybridization" refers to a technique that provides for genetic comparisons integrated over the entire genome of two species.

GenBank—The term "GenBank" refers to the NIH genetic sequence database, an annotated collection of all publicly available DNA sequences. GenBank is part of the International Nucleotide Sequence Database Collaboration, which is comprised of the DNA DataBank of Japan (DDBJ), the European Molecular Biology Laboratory (EMBL), and GenBank at the National Center for Biotechnology Information. Each GenBank entry includes a concise description of the sequence, the scientific name and taxonomy of the source organism, and a table of features that identifies coding regions and other sites of biological significance, such as transcription units, sites of mutations or modifications, and repeats.

Gram-positive—The term "gram positive" refers to bacteria that are stained dark blue or violet by gram staining, in contrast to gram negative bacteria which are not stained dark blue or violet by gram staining. The stain is caused by a higher amount of peptidoglycan in the cell wall, which typically lacks the secondary membrane and lipopolysaccharide layer found in other bacteria.

(2) Introduction

This specification describes *Bacillus pumilus* SAFR-032, isolated from the surface in a spacecraft assembly facility, whose round spores are resistant to Ultra Violet (UV) and gamma radiation, Hydrogen Peroxide ($H_2O_2$) and desiccation. The *Bacillus* strain isolated and described herein was characterized based on a polyphasic taxonomic approach that examined its phenotypic and genotypic affiliations. It is readily apparent to those skilled in the art that within nature, various modifications and variations occur to any given organism and that the description described herein may be altered to account for any modifications or variations.

The strain disclosed in this description will be deposited in an international depository, under conditions that assure that access to the cultures will be available during the pendency of this patent application to one determined by the Commissioner of Patents and Trademarks to be entitled thereto under 37 C.F.R. 1.14 and 35 U.S.C. 122. The strain disclosed in this description has been deposited in the American Type Culture Collection (ATCC), 10801 University Blvd., Manassas, Va. 20110 U.S.A. as PTA-7603. The deposit was received by the ATCC on May 19, 2006 and was given an accession number by the International Depository Authority of PTA-7603. The deposit has been made to and received by the International Depository Authority under the provisions of the Budapest Treaty, and all restrictions upon public access to the deposit will be irrevocably removed upon the grant of a patent on this application. The deposits will be available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested due to the condition of the deposit(s).

Several surveys on the microbial diversity of spacecraft assembly facilities over a period of 3 years have lead to the repeated isolation of *Bacillus pumilus* strains. Of these strains tested, *B. pumilus* SAFR-032 spores were the most resistant to UV irradiation (254 nm; FIG. 1) and the total flux at the Mars simulated solar constant. Spores of *B. pumilus* SAFR-032 showed highest resistance to all three UV bandwidths. LD90 of *B. pumilus* SAFR-032 under Mars solar UV simulated solar constant was >360 sec, about 10 times greater than *B. subtilis* 168 (FIG. 2). *B. pumilus* SAFR-032 spores are 2 to 3 times and ten times more resistant than a previously patented "hardy" *B. odysseyi* spores to UV 254 nm and Mars UV simulated solar constant, respectively. *B. pumilus* is more resistant than any bacterium reported in the literature to date.

It follows that standard UV treatments which are effective against *B. subtilis* spores may not be sufficient to inactivate all spores such as SAFR-032. Hence the spores of *B. subtilis* can not be reliably used as a biodosimetry model for the UV inactivation of spores. SAFR-032 spores also exhibited resistance to H202. Upon exposure to 5% liquid H202 SAFR-32 spores experienced a 2 log decrease in population compared to 4 log reduction exhibited by *B. subtilis* 168 spores. In addition, *B. pumilus* SAFR-032 spores were resistant to 0.5 Mrad gamma-radiation (25 rad/sec).

The goal of planetary protection as stated in NASA policy is the prevention of forward and backward contamination. This policy applies directly to the control of terrestrial organisms contaminating spacecraft intended to land, orbit, flyby or be in the vicinity of extraterrestrial bodies. Planetary Protection protocols for the non-life detection Mars landing missions such as, Mars Exploration Rovers (MER), did not require that the rovers be heat-sterilized prior to launch. Instead, NASA relied on a series of sequential sterilization steps using alcohol to maintain the cleanliness of the MER vehicles. The question is whether forward contamination will be significantly increased by the current approach to spacecraft sanitation such as used for the MARS landers.

Spores of *Bacillus subtilis* have been shown to survive up to 6 years under interstellar space conditions. However, only shielding from UV radiation enabled *B. subtilis* endospores to survive the conditions long term. The solar flux at the Martian surface is considerably less than interstellar space and there is the potential that atmospheric conditions could further attenuate UV radiation. In order to examine the germicidal effects of direct UV irradiation predicted for equatorial Mars, spores were exposed to irradiation while in aqueous solutions, and or while deposited to spacecraft surfaces. B. pumilus SAFR-032 is 10× more resistant to UV radiation than B. subtilis. It follows that organisms able to survive in this environment may exhibit resistance to other perturbations. In addition, it has previously been suggested that the organisms associated with the facilities where assembly and encapsulation activities take place will indicate likely contamination of the spacecraft. Studies that follow existing planetary protection microbial isolation procedures that involve a heat-shock step have shown spore-formers to be the most common type of microbes isolated from surfaces of various spacecraft. Since most of the published information was based on the laboratory strains, predicting the actual survival and possible adaptation of terrestrial life on Mars is limited due to the lack of robust empirical data on the survival of indigenous spacecraft microbes to the Martian UV conditions. Previous studies have used model dosimetric strains to represent the potential survival of organisms under ~200 J/m2 UVC (14) and Mars solar UV irradiation conditions. The present invention produces data that indicates spores of B. pumilus SAFR-032 are far more resistant to Mars solar UV irradiation conditions than these model dosimetric strains. It may be necessary to consider these resistant organisms when investigating the survival of microorganisms under outer space or the Martian conditions.

The search for life on other planets will involve ultra-sensitive technologies that detect cells and biomarkers. Contamination of extraterrestrial bodies with cells or biomarkers originating from Earth (forward contamination) would seriously compromise the interpretation that life signatures. Recent data indicate the routine meteorite exchange between Earth and Mars and living microbes, particularly bacterial spores, may survive interplanetary transfer. Consequently, current planetary protection protocols require that spacecraft be constructed and assembled under conditions as nearly as possible approaching sterility. To achieve these conditions, robotic spacecraft are assembled in clean rooms where air circulation is controlled and strict hygienic practices are implemented to minimize microbial contamination. In addition a number of sterilants including vaporous hydrogen peroxide (H2O2) and ultraviolet radiation (UV) are under consideration. As part of the NASA planetary protection program, recent monitoring of microbial diversity in the relatively extreme environment (low nutrient, controlled humidity, periodic disinfection) NASA JPL-SAF resulted in the isolation of a number of microbial species inhabiting various parts of the facility. The predominant strains of spore-forming bacteria identified by biochemical testing and 16S rDNA analysis as being most closely related to Bacillus pumilus. Not only were B. pumilus spores found to survive in the JPL-SAF, but were also recently recovered from hardware surfaces and air particles aboard the International Space Station (ISS). It follows that spores of B. pumilus are capable of escaping current spacecraft disinfection regimens and may be inadvertently transported into space.

A key element of spore resistance is a multilayered protein shell that encases the spore called the spore coat. The coat of the best-studied spore-forming microbe, B. subtilis, is comprised of at least 45 proteins, most of which are poorly characterized. Several protective roles for the coat are well characterized, including resistance to large toxic molecules, ortho-phthalaldehyde, and UV radiation. It has only recently been shown that SAFR-032 can be mixed with UV susceptible species such as B. subtilis 168, allowing the susceptible species to survive longer (FIG. 3). These results make a strong argument that the physical makeup of SAFR-032 rather than biochemical reactions is responsible for its heightened resistance.

A goal associated with the present invention is to produce new strategies for inactivating resistant organisms like SAFR-032. Identifying the particular component of the spore that allows this heightened resistance can guide the development of sterilization procedures that are targeted to the specific molecules responsible for resistance, and avoid using unduly harsh methods that jeopardize equipment. An important specific long-term goal is an improved sterilization procedure that will enable NASA to meet planetary protection requirements without a terminal heat sterilization step. This would support implementation of planetary protection policies for life detection missions.

Typically hospitals and government agencies use biological indicators to ensure the quality control of sterilization processes (http://www.ravenlabs.com/bis.html). The spores of SAFR-032 that are more resistant to several sterilization procedures would serve as a better biological indicator than those in use currently.

Figure 5:
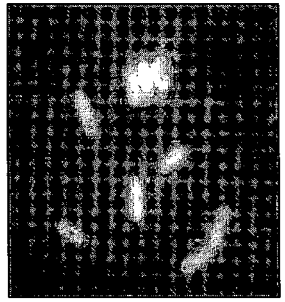
FIG. 5 is a light microscopy image of *Bacillus pumilus* SAFR-032 spores.
Figure 6:
FIG. 6 is a transmission electron microscopy image of *Bacillus pumilus* SAFR-032 spores.

As such, the present invention comprises an isolated biologically pure culture of Bacillus pumilus SAFR-032, under GenBank accession number AY167879. For further illustration, FIGS. 4, 5, and 6 illustrate micrograph images of the Bacillus pumilus SAFR-032 spores.

For a further description of B. pumilus SAFR-032, including both a phenotypic and genotypic description, see Appendices A, B, and C. Appendices A, B, and C are incorporated herein as though set forth fully herein. As can be appreciated by one in the art, the Appendixes provide an enabling description of the isolation and classification of B. pumilus SAFR-032.

What is claimed is:

1. An isolated biologically pure culture of Bacillus pumilus SAFR-032 deposited under ATCC accession number PTA-7603.

* * * * *